United States Patent

Hamersma et al.

[11] Patent Number: 5,854,235
[45] Date of Patent: Dec. 29, 1998

[54] 17-SPIROMETHYLENE STEROIDS

[75] Inventors: Johannes Antonius Maria Hamersma; Everardus Otto Maria Orlemans; Johannes Bernardus Maria Rewinkel, all of Oss, Netherlands

[73] Assignee: Akzo Nobel N.V., Arnhem, Netherlands

[21] Appl. No.: 962,798

[22] Filed: Nov. 3, 1997

Related U.S. Application Data

[62] Division of Ser. No. 98,665, Jul. 28, 1993, Pat. No. 5,712,264.

[30] Foreign Application Priority Data

| Jul. 29, 1992 | [EP] | European Pat. Off. | 92202339 |
| Jun. 10, 1993 | [EP] | European Pat. Off. | 93201657 |

[51] Int. Cl.$^6$ .......... A61K 31/58; A01N 43/80; C07J 21/00; C07J 71/00
[52] U.S. Cl. .......... 514/173; 514/379; 514/403; 514/462; 540/9; 540/23; 540/28; 548/241; 548/242; 548/357.5; 549/331; 549/332
[58] Field of Search .......... 540/28, 9, 23; 549/331, 332; 548/241, 242, 357.5; 514/173, 379, 403, 462

[56] References Cited

U.S. PATENT DOCUMENTS

| 2,744,122 | 5/1956 | Djerassi et al. | 260/397.4 |
| 3,280,157 | 10/1966 | Legatt et al. | 260/397.4 |
| 3,338,892 | 8/1967 | Farkas | 260/239.55 |
| 3,478,067 | 11/1969 | Bertin et al. | 260/397.3 |
| 3,764,596 | 10/1973 | Galantay | 260/239.55 |
| 3,927,046 | 12/1975 | van den Broek | 260/397.3 |
| 4,081,537 | 3/1978 | Hofmeister et al. | 424/238 |
| 4,386,085 | 5/1983 | Teutsch et al. | 424/238 |
| 5,292,878 | 3/1994 | Hamersma et al. | 540/28 |

FOREIGN PATENT DOCUMENTS

| 623844 | 10/1961 | Belgium . |
| 0116974 | 8/1984 | European Pat. Off. . |
| 0277089 | 8/1988 | European Pat. Off. . |
| 0289073 | 11/1988 | European Pat. Off. . |
| 0321010 | 6/1989 | European Pat. Off. . |
| 0404283 | 12/1990 | European Pat. Off. . |
| 7302540 | 9/1973 | Netherlands . |
| WO 8705908 | 10/1987 | WIPO . |

OTHER PUBLICATIONS

M. Mori et al., *J. Org. Chem.,* 48:4058–4067, 1983.
D. Gange et al., *Journal of American Chemical Society,* 100:24:7746–7747.

*Primary Examiner*—Mukund J. Shah
*Assistant Examiner*—Bruck Kifle
*Attorney, Agent, or Firm*—Mary E. Gormley

[57] ABSTRACT

The invention relates to a steroid derivative which steroidal skeleton is bound at carbon atom 17 to a spiromethylene ring of the formula:

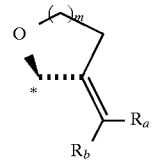

wherein $R_a$ and $R_b$ are independently selected from the group consisting of hydrogen, methyl, and halogen; m is 1 or 2; and the asterisk denotes carbon atom 2 of the spiromethylene ring which is carbon atom 17 (or carbon atom 17α of a homosteroid skeleton) of the steroid. The steroids have progestational or antiprogestational activity.

4 Claims, No Drawings

17-SPIROMETHYLENE STEROIDS

This application is a division, of application Ser. No. 08/098,665 filed Jul. 28, 1993 now U.S. Pat. No. 5,712,261.

The invention relates to 17-spirorethylene steroids, their preparation, pharmaceutical compositions containing the same, their use for contraception, and their use for the manufacture of a medicament.

Many progestational and antiprogestational steroids are known. It is now found that the activity of these steroids can be dramatically improved by the introduction of a new 17-substituent. It was found that this priciple holds for both progestational and anti-progestational compounds, for example in comparison with steroids having the classical 17β-hydroxy-17α-ethynyl substituents.

The present invention relates to a steroid derivative of which carbon atom 17 (or carson atom 17α of a homosteroid skeleton) is carbon atom 2 of a spiromethylene ring of the formula:

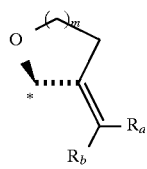

wherein $R_a$ and $R_b$ are independently selected from the group consisting of hydrogen, nethyl, and halogen; m is 1 or 2; and the asterisk denotes carbon atom 2 of the spiromethylene ring which is carbon atom 17 of the steroid (or carbon atom 17α of a homosteroid skeleton).

More specifically the steroid derivatives are claimed wherein the steroidal skeleton has the formula:

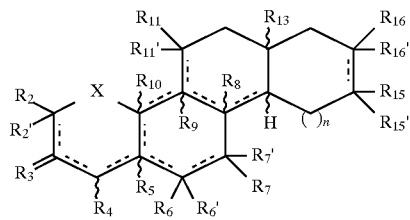

wherein n is 0 or 1;

X is $CHR_1$ or a bond;

$R_1$ is H, $CH_3$, CN, OH, Oacyl, F, spirocyclopropyl, or together with $R_2$ or $R_{10}$ $CH_2$, $CF_2$, or $OC(CH_3)_2O$, or together with $R_{11}$ $CH_2O$;

$R_2$ is H, alkyl, $CH_2OH$, CN, OH, Oacyl, F, spirocyclopropyl, or together with $R_1$ or $R_3$ the groups indicated in the definitions of $R_1$ and $R_3$ respectively, or together with $R_{10}$ $CH_2$, or together with $R_2$, =CH—R, wherein R is H, OH, Oalkyl, or Oacyl;

$R_2$, is H, alkyl, or CN, or Together with $R_2$ the groups indicated in the definition of $R_2$;

$R_3$ is $H_2O$, NOH, NOalkyl, NOacyl, (H,OH), (H,Oacyl), (O,Oalkyl), (H,Ocycloalkyl), or 1-pyrrolidinyl, or (O,alkynyl) when X is a bond, or $R_2$ and $R_3$ together with $C_2$ and $C_3$ of the steroid skeleton form an oxazole:

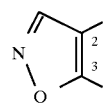

or a diazole:

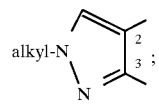

$R_4$ is H, alkyl, halogen, CN, $N_3$, OH, phenylmethyl, phenylthiomethyl, methylthio, or alkylcarbonylthio;

$R_5$ is H or OH;

One of $R_6$ and $R_7$ is 11, alkyl, $CF_3$, $CH_2F$, OH, halogen, CN, Oalkyl, Oacyl, Sacyl, $CH_2OH$, $NO_2$, COOalkyl, $OSO_2$alkyl, or spirocyclopropyl, and the other is H, or $R_6$ together with $R_7$ is $CH_2$, $CF_2$, O, CHClCHICl, or $R_6$ together with $R_6$, is $CH_2$ when $R_7$ is H, or $R_7$ together with $R_7$, is $CH_2$ or $CF_2$ when $R_6$ is H;

$R_6$, is H, or H or alkyl when $R_6$ is alkyl, or H or halogen when $R_6$ is halogen, or together with $R_6$ the groups indicated in the definition of $R_6$, or H or F when $R_6$ and $R_7$ are together $CF_2$;

$R_7$, is H, or H or alkyl when $R_7$ is alkyl, or H or halogen when $R_7$ is halogen, or together with $R_7$ the groups indicated in the definition of $R_7$;

$R_8$ is H or $CH_3$;

$R_9$ is H, halogen, OH, or methyl, or together with $R_{10}$ $CH_2$ or O;

$R_{10}$ is H, alkyl, halogen-substituted alkyl, alkenyl, alkynyl, halogen, OH, OOH, OOacyl, Oalkyl, Oalkynyl, amino, alkyl-substituted amino, NHacyl, aminomethyl, alkyl substituted aminomethyl, CHO, COOH, COOalkyl, $CH_2OH$, $CH_2Oacyl$, $CH_2CH_2OH$, or together with $R_1$, $R_9$, or $R_{11}$, the groups indicated in the definition of $R_1$, $R_9$, and $R_{11}$, respectively, or together with C10, C9, C11 of the steroid skeleton, and $R_{11}$, when R11 is an aryl or heteroaryl, a 6-membered ring;

$R_{11}$ is H, alkyl, cycloalkyl, alkenyl, alkynyl, phenyl-ethyl, arylethynyl, heteroarylethynyl, halogen-substituted alkyl, alkyl-substituted aminoalkyl, halogen, $CH_2OCH_3$, OH, OOH, Oalkyl, Oacyl, SH, Salkyl, $N_3$, $Si(CH_3)_2$, aryl, or heteroaryl, or $R_{11}$, together with $R_{11}$, is $CH_2$, $CF_2$, or CHF, or together with $R_{10}$ OC=O or OCHF, or together with $R_1$ $OCH_2$, or together with $R_{13}$ $OCH_2$ or $CH_2CH_2CH_2$;

$R_{11}$, is H, alkyl, cycloalkyl, alkenyl, alkynyl, phenyl-ethyl, arylethynyl, heteroarylethynyl, halogen-substituted alkyl, alkyl-substituted aminoalkyl, halogen, $CH_2OCH_3$, OH, OOH, Oalkyl, Oacyl, SH, Salkyl, $N_3$, $Si(CH_3)_2$, aryl, or heteroaryl, or $R_{11}$, together with $R_{11}$ the groups indicated in the definition of $R_{11}$, or together with $R_{13}$ $CH_2CH_2CH_2$ when $R_{11}$ is H;

$R_{13}$ is H, alkyl, alkenyl, alkynyl, fluoro-substituted alkyl, phenyl, or cycloalkyl, or $R_{13}$ together with $R_{11}$, $R_{11}$, or $R_{16}$ is $CH_2CH_2CH_2$;

One of $R_{15}$ and $R_{16}$ is H, OH, Oalkyl, Oacyl, halogen, alkyl, or spirocyclopropyl, and the other is H, or $R_{15}$ together with $R_{16}$ is $CH_2$ or CClF;

$R_{15}$, is H or together with $R_{15}$ $CH_2$ or $F_2$ when $R_{16}$ is H;

$R_{16'}$ is H or together with $R_{16}$ $CH_2$ or $F_2$ when $R_{15}$ is H; the twitched lines represent an α or β bond; and the dotted lines represent up to four optional non-adjacent bonds; or pharmaceutically acceptable salts thereof.

Preferred steroid derivatives according to the invention have above-mentioned structure wherein:

n is 0;

X is $CHR_1$;

$R_1$, $R_2$, $R_{2'}$, $R_4$, $R_5$, $R_{6'}$, $R_{7'}$, $R_8$, $R_9$, $R_{15}$, and $R_{16}$, are H;

$R_3$ is $H_2$, O, (H,OH), NOH;

$R_6$ and $R_7$ are H, or one of $R_6$ and $R_7$ is H and the other is $CH_3$, or $R_6$ together with $R_7$ is $CH_2$;

$R_{10}$ is H or $CH_3$, or together with $R_1$ $CH_2$;

$R_{11}$ is H, alkyl, vinyl, ethynyl, phenylethynyl, phenyl which is substituted at its 4 position with CN, acyl, alkylthio, alkoxyalkyl, amino or alkyl-substituted amino, or an N-oxide of the amino or alkyl-substituted amino, or $R_{11}$ together with $R_{11'}$ is $CH_2$, $CF_2$, or CHF;

$R_{11'}$ is H, alkyl, vinyl, ethynyl, phenylethynyl, phenyl which is substituted at its position 4 with CN, acyl, alkoxyalkyl, amino or alkyl-substituted amino, or an N-oxide thereof, or $R_{11'}$ together with $R_{11}$ is $CH_2$, $CF_2$, or CHF;

$R_{13}$ is alkyl;

$R_{15}$ and $R_{16}$ are each H or together $CH_2$; the 13 bond is β and the 14 bond is α; and positions 4–5; 4–5,8–9; 4–5,9–10; 4–5,15–16; 5–10; 3–4; or 4–5,6–7 of the steroid skeleton may have an additional bond.

More preferred are the steroid derivatives having above-mentioned steroid structure wherein $R_a$ and $R_b$ are independently selected from the group consisting of hydrogen, methyl, and halogen (preferably chlorine);

n is 0;

X is $CHR_1$;

$R_1$, $R_2$, $R_{2'}$, $R_4$, $R_5$, $R_{6'}$, $R_{7'}$, $R_8$, $R_9$, $R_{10}$, $R_{13}$, $R_{15}$, $R_{15'}$, $R_{16}$, and $R_{16'}$ are H;

$R_3$ is $H_2$, O, (H,OH), or NOH;

$R_6$ and $R_7$ are H, or one of $R_6$ and $R_7$ is H and the other is $Ch_3$, or $R_6$ together with $R_7$ is $CH_2$;

$R_{11}$ is H, $CH_3$, $CH_2=CH$, or phenyl, the 4 position of which is substituted with dimethylamino, vinyl, acetyl, methoxy, methylthio, oxazole, CN, CHO, CHNOH, or CONR'R", R' and R" being independently H, alkyl, or hydroxy-substituted alkyl, or $R_{11}$ together with $R_{11'}$ is $CH_2$, CHF, or $CF_2$;

$R_{11'}$ is H or together with $R_{11}$ $CH_2$, CHF, or $CF_2$;

$R_{13}$ is $CH_3$, $C_2H_5$, or $C_3H_7$; the 13 bond is α and the 14 bond is α; and positions 4–5; 4–5,8–9; 4–5,9–10; 4–5,15–16; 5–10; 3–4; or 4–5,6–7 of the steroid skeleton may have an additional bond.

Most preferred are the steroid derivatives wherein n is 0;

X is $CHR_1$;

$R_1$, $R_2$, $R_{2'}$, $R_4$, $R_5$, $R_6$, $R_{6'}$, $R_7$, $R_{7'}$, $R_8$, $R_9$, $R_{10}$, $R_{11'}$, $R_{13'}$, $R_{15}$, $R_{15'}$, $R_{16}$, and $R_{16'}$ are H;

$R_3$ is O;

$R_{11}$ is p-dimethylamino-, p-acetyl- or p-methylthio-substituted phenyl; the 13 bond is β and the 14 bond is α; and positions 4–5; 4–5,15–16; or 4–5,9–10 of the steroid skeleton have an additional bond.

The term alkyl means a branched or unbranched alkyl group having 1–8 carbon atoms, such as methyl, ethyl, propyl, isopropyl, butyl, tert-butyl, pentyl, hexyl and the like. Preferred alkyl groups have 1–4 carbon atoms, and most preferred is the methyl group.

The term acyl means an acyl group derived from an alkylcarboxylic acid, the alkyl moiety having the previously given meaning.

The term alkenyl means a branched or unbranched alkenyl group having 2–6 carbon atoms. Preferred are alkenyl groups having 2–4 carbon atoms, like vinyl.

The term alkynyl means a branched or unbranched alkynyl group having 2–6 carbon atoms. Preferred are alkynyl groups having 2–4 carbon atoms, like ethynyl and 1-propynyl.

The term cycloalkyl means a cycloalkyl group having 3-carbon atoms like cyclopropyl, cyclopentyl and cyclohexyl.

The term halogen means fluorine, chlorine, bromine or iodine. Chlorine is the preferred halogen.

The term aryl means an aryl group like phenyl and naphthyl. Heteroaryl groups are heteroaromatic groups like pyridinyl, pyrimidinyl, thienyl or non-hetero-aromatics condensed with heteroaromatic groups. The aryl, heteroaryl and the phenyl groups used in the definition of the steroids of the inventions may be substituted by alkyl, Oalkyl, halogen, acyl and OH, as previously defined. The 11-phenyl group may also be substituted by amino, alkyl-substituted amino (preferably dimethylamino) or an N-oxide of the amino or alkyl-substituted amino group, vinyl, methylthio, oxazole, CN, CHO, CHNOH, CONR'R", R' and R" being independently H, alkyl, or hydroxy-substituted alkyl. The oxazole may also be an alkyl substituted oxazole.

The first orally active progestagens are norethisterone and derivatives thereof (U.S. Pat. No. 2,744,122). These first-generation progestagens have a 17α-ethynyl substituent and, apart from the 3-keto-delta$^{4,5}$, no further substituents. These compounds have low progestagenic and low androgenic activity, and a low selectivity. Derivatives like norethisterone acetate and nor-ethynodrel show very low estrogenic activity and low SHBG binding affinity. Second-generation progestagens were found having in addition a 18-methyl substituent. The most pertinent representative of this series is (levo)norgestrel (Belgian patent 623,844), which shows a better progestagenic activity, but also an increased androgenic activity. The selectivity is, therefore, not really improved with respect to the first-generation progestagens. The second-generation progestagens show no estrogenic activity, have a slight glucocorticoid activity and an increased SHBG binding affinity. The third-generation compounds have two additional substituents. The most remarkable representatives are desogestrel (U.S. Pat. No. 3,927,046) having an 11-methylene group, and gestodene (U.S. Pat. No. 4,081,537) having a delta$^{15, 16}$ double bond. These compounds have a better selectivity because their progestagenic activity is increased whereas their androgenic activity is similar or decreased with respect to levonorgestrel. Apart from their progestagenic activity, these compounds have at least one other hormonal activity, like glucocorticoid, antimineralocorticoid or estrogenic activity. The progestagenic compounds of the present invention are the fourth-generation of progestagens, having a pure progestagenic profile, without significant androgenic or other hormonal activities. Most compounds have no glucocorticoid activity, but some compounds having m is 2 show weak glucocorticoid activity. The compounds of this invention show an extremely strong binding affinity to the progesterone receptor.

The first-generation antiprogestagens are weakly active compounds like RMI 12,936 (Dutch pat. 7302540) and R-2323 (Gestrinone; U.S. Pat. No. 3,478,067). High antiprogestagenic activity was found with the second-generation of compounds, the lead compound of which is RU 486 (Mifepristone; U.S. Pat. No. 4,386,085). These compounds typically have an 11-aryl group, usually phenyl substituted with a para-dimethylamino group, and a 17α-1-propynyl group. Third-generation antiprogestational compounds have an additional substituent, mostly a 6- or 7-methyl group, and sometimes have a 17 spiro-ether group. Examples are Org 61710 (U.S. Pat. No. 4,871,724) and Org 31806 (U.S. Pat. No. 4,921,845). These compounds have diminished antiglucocortcoid activity. The antiprogestagenic compounds of the present invention are the fourth-generation of antiprogestagens, having a pure antiprogestagenic profile, without other significant hormonal activities. These compounds show an extremely strong binding affinity to the progesterone receptor.

The steroids of this invention, being a new generation of progestational and antiprogestational steroids, have improved affinity to the progesterone receptor, and/or have improved selectivity. These improved properties lead to better therapeutic effects on administering the compounds in patients.

The progestagenic and antiprogestagenic steroids of this invention can be used as contraceptives. They further exhibit the normal activities known for progestagens and antiprogestagens, such as treatment of menstrual disorders and hormone dependent tumors.

The steroids of the invention having m is 1 may be prepared by treating any 17-keto steroid (the reactive substituents of which are protected in a manner as usual for the protection of reactive groups) with alkylOCLi=C=CH$_2$ wherein alkyl is a lower alkyl, preferably methyl, using, for example, the method of D. Gange and Ph. Magnus, J. Am. Chem. Soc. 100 (1978), 7747–7748. The 17-allenyl derivative obtained is treated with a base, preferably potassium tert-butoxide, in a suitable solvent (for example tert-butanol) or with silver nitrate to cotain the alkyl enol ether of a furan ring, carbon atom 2 of which is carbon atom 17 of the steroid skeleton (or carbon atom 17α for a homosteroid). Acid treatment of this compound gives the furan-3-one ring, carbon atom 2 of which is carbon atom 17 of the steroid skeleton (or carbon atom 17α for a homosteroid). When necessary, groups cleaved during the reaction are protected again, after which a Wittig, Wittig-Horner, or similar reaction is performed (for instance a Peterson reaction) with W-CHR$_a$R$_b$ wherein R$_a$ and R$_b$ have the previously given meanings, and W is a group suitable for a Wittig(like) or Peterson reaction, for instance a trimethyl- or triphenylphosphorane group (i.e. giving for instance (C$_6$H$_5$)$_3$(halogen) PCHR$_a$R$_b$ or the Peterson reagent (CH$_3$)$_3$Si(Mghalide) CHR$_a$R$_b$), after which the remaining protective groups, when present, are removed and the compound obtained is optionally converted into a pharmaceutically acceptable salt.

The steroids of the invention having m is 2 may be prepared by treating any 17-keto steroid (other reactive substituents of which are protected in a manner as usual for the protection of reactive groups) with a pentenol derivative R$_a$R$_b$C=CLi—CH$_2$—CH$_2$—CH$_2$—OSi(alkyl)$_3$, wherein R$_a$, R$_b$ and alkyl have the previously given meanings, and which can be prepared by methods known in the art from the corresponding 2-bromo-5-hydroxy-1-pentene derivative, which is prepared, for example by the method of M. Mori et.al., J. Org. Chem. 48, 4058 (1983), followed by acid hydrolysis to give the 17,24-dihydroxy-steroid, after which the 24-hydroxy group is converted into a leaving group, for instance into a mesylate by treatment with methanesulfonylchloride, followed by ring closure to the 17-spiroether derivative by heating, for example, in toluene with a base such as s-collidine, after which the remaining protecting groups, when present, are removed and the compound obtained is optionally converted into a pharmaceutically acceptable salt.

The novel compounds may be isolated from the reaction mixture in the form of a pharmaceutically acceptable salt. The pharmaceutically acceptable salts may also be obtained by treating the free base with an organic or inorganic acid such as HCl, HBr, HI, H$_2$SO$_4$, H$_3$PO$_4$, acetic acid, propionic acid, glycolic acid, maleic acid, malonic acid, methanesulphonic acid, fumaric acid, succinic acid, tartaric acid, citric acid, benzoic acid, and ascorbic acid.

The compounds of the invention may be administered enterally or parenterally, and for humans preferably in a daily dosage of 0,00025-10 mg per kg body weight. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray. For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

The invention is further illustrated by the following examples.

EXAMPLE 1

(17α)-17,23-epoxy-24-norchola-4,20-dien-3-one was prepared from the known (17β)-4',5'-dihydrospiro-[androst-4-ene-17,2'(3' H)-furan]-3,3'-dione (see D. Gange and Ph. Magnus, J. Am. Chem. Soc. 100, 7747–7748 (1978)) as follows:

(i) 6.64 g of the above-mentioned dione were dissolved in 13.5 ml of absolute ethanol under a nitrogen atmosphere. The reaction mixture was cooled in an ice bath and 7 ml of triethyl orthoformate and 70 mg of p-toluenesulfonic acid were added, after which the reaction mixture was stirred at 0° C. for 5 h. The reaction was stopped by addition of 2 ml of triethylamine, and 4 ml of water were added. The resulting precipitate was filtered off, yielding 6.7 g (93%) of crystalline (17β)-3-ethoxy-4',5'-dihydrospiro-[androsta-3,5-diene-17,2'(3' H)-furan]-3'-one.

(ii) To a suspension of 18.7 g of potassium tert-butoxide in 290 ml of toluene under a nitrogen atmosphere were added 70 g of methyltriphenyl-phosphonium bromide. The mixture was refluxed for 45 min and then cooled. 6.7 g of the above-mentioned dienone were added and the mixture was refluxed for 2.5 h. The mixture was subsequently poured into ice-water, the toluene layer separated, washed with brine, dried over sodium sulfate and concentrated under reduced pressure. The residue was chromato-graphed to afford 3.53 g (53%) of pure (17β)-17,23-epoxy-3-ethoxy-24-norchola-3,5,20-triene.

(iii) 3.53 g of the above-mentioned triene were dissolved in 36 ml of dichloromethane. To this solution were added 3.6 ml of 6N hydrochloric acid, and the mixture was stirred vigorously for 1.5 h. The reaction mixture was then poured into 360 ml of ice-water, the organic layer separated, dried over sodium sulfate and concentrated under reduced pressure to afford 2.46 g (75%) of (17α)-17,23-epoxy-24-norchola-4,20-dien-3-one after recystallization from ethyl acetate. M.p. 127.2° C. $[\alpha]_D^{20}$=+10.5° (c=0.99, chloroform).

EXAMPLE 2

In a manner similar to Example 1 were prepared:

(17α)-17,23-epoxy-19,24-dinorchola-4,20-dien-3-one from (17α)-4',5'-dihydrospiro[estr-4-ene-17,2'(3' H)-furan]-3,3'-dione. M.p. 130.3° C. $[\alpha]_D^{20}$=−47.4° (c=0.95, chloroform).

(17α)-17,23-epoxy-13-ethyl-18,19,24-trinorchola-4,20-dien-3-one from (17'β)-13'-ethyl-4,5-dihydrospiro[furan-2(3 H),17'-gon[4]ene]-3,3'-dione. M.p. 135.0° C. $[\alpha]_D^{20}$=−63.9° (c=1.04, chloroform).

(17α)-17,23-epoxy-11-methylene-19,24-dinorchola-4,20-dien-3-one from (17β)-4',5'-dihydro-11-methylenespiro-[estr-4-ene-17,2'(3' H)-furan]-3,3'-dione. M.p. 176.5° C. $[\alpha]_D^{20}$=+64.3° (c=1.0, chloroform).

(17α)-17,23-epoxy-13-ethyl-11-methylene-18,19-24-trinorchola-4,20-dien-3-one from (17'β)-13'-ethyl-4,5-dihydro-11'-methylenespiro[furan-2(3 H),17'-gon[4]ene]-3,3'-dione. M.p. 173.5° C. $[\alpha]_D^{20}$=+50.7° (c=1.02, chloroform).

(17α)-17,23-epoxy-19,24-dinorchola-4,9,20-trien-3-one from (17β)-4',5'-dihydrospiro[estra-4,9-diene-17,2'(3' H)-furan]-3,3'-dione. The amorphous solid obtained melted at 136° C. and had an $[\alpha]_D^{20}$ of −280°(c=1.0, dioxane).

(17α)-17,23-epoxy-19,24-dinorchola-4,15,20-trien-3-one from (17β)-4',5'-dihydrospiro[estra-4,15-diene-17,2'(3' H)-furan]-3,3'-dione. M.p. 137° C. $[\alpha]_D^{20}$=−194.8° (c=1.0, chloroform).

(17α)-17,23-epoxy-13-ethy-18,19,24-trinorchola-4,15,20-trien-3-one from (17'β)-13'-ethyl-4,5-dihydrospiro-[furan-2(3 H),17'-gona-4,15-diene]-3,3'-dione. M.p. 136.4° C. $[\alpha]_D^{20}$=−194.2° (c=0.99, chloroform).

(6α,17α)-17,23-epoxy-6-methyl-19,24-dinorchola-4,20-dien-3-one from (6α,17β)-4',5'-dihydro-6-methylspiro-[estr-4-ene-17,2'(3' H)-furan]-3, 3'-dione. M.p. 105.9° C. $[\alpha]_d^{20}$=−89.8° (c=1.035, dioxane).

(7α,17α)-17,23-epoxy-7-methyl-19,24-dinorchola-5(10),20-dien-3-one from (7α,17β)-4',5'-dihydro-7-methylspiro-[estr-5(10)-ene-17,2'(3' H)-furan ]-3,3'-dione. Careful hydrolysis (oxalic acid in water) of the intermediate afforded the desired product as an amorphous solid. $[\alpha]_D^{20}$=+61.4° (c=0.975, chloroform).

(7α,17α)-17,23-epoxy-7-methyl-19,24-dinorchola-4,20-dien-3-one from (7α,17β)-4',5'-dihydro-7-methylspiro-[estr-5(10)-ene-17,2'(3' H)-furan ]-3,3'-dione. Hydrolysis under more strenuous conditions than in the previous reaction (hydrochloric acid in acetone) of the intermediate afforded the desired product. M.p. 127.6 ° C. $[\alpha]_D^{20}$=−20.5° (c=1.0, chloroform).

(11α,17β)-17,23-epoxy-11-methyl-19,24-dinorchola-3,20-dien-4-one from (11β,17β)-4',5'-dihydro-11-methylspiro-[estr-4-ene-17,2'(3' H)-furan]- 3,3'-dione. M.p. 181° C. $[\alpha]_D^{20}$=−14.6° (c=1.0, chloroform).

(3' E,17β)-3'-ethylidene-4',5'-dihydrospiro[estra-4-ene-17,2'(3' H)-furan]-3-one from (17β)-4',5'-dihydro-spiro-[estra-4-ene-17,2'(3' H)-furan]-3,3'-dione by treatment of the intermediate (17β)-3-ethoxy-4',5'-dihydrospiro-[estra-3,5-diene-17,2'(3' H)-furan]-3'-one with ethyltri-phenylphosphonium bromide. M.p. 143.6° C. $[\alpha]_D^{20}$=−32.0° (c=1.0, chloroform).

(17α,21E)-21-chloro-17,23-epoxy-19,24-dinorchola-4,20-dien-3-one from (17β)-4',5'-dihydrospiro[estr-4-ene-17,2'(3' H)-furan]-3,3'-dione by treatment of the intermediate (17β)-3-ethoxy-4',5'-dihydrospiro[estra-3,5-diene-17,2'(3' H)-furan]-3'-one with chloromethyl-triphenylphosphonium chloride. M.p. 156.8° C. $[\alpha]_D^{20}$=−16.8° (c=0.5, chloroform).

(17α)-17,23-epoxy-11-methylene-19,24-dinorchola-4,15,20-trien-3-one from (17β)-4',5'-dihydro-11-methylenespiro-[estr-4-ene-17,2'(3' H)-furan]-3,3'-dione. M.p. 183.7° C. $[\alpha]_D^{20}$=−82.7° (c=1.0, chloroform).

EXAMPLE 3

(17α)-17,23-epoxy-13-ethyl-11-methylene-18,19,24-trinorchola-4,20-diene was prepared directly from (17'α)-13'-ethyl-4,5-dihydro-11'-methylenespiro[furan-2(3 H),17'-gon-4-ene]-3-one by reaction with methyltri-phenylphosphonium bromide as described in Example 1(ii). M.p. 138.4° C. $[\alpha]_D^{20}$ =+10.4° (c=0.99, chloroform).

EXAMPLE 4

In a similar manner as in Example 3 the following compounds were prepared:

(5α,17α)-17,22-epoxy-13-ethyl-11-methylene-18,19,24-trinorchola-3,20-diene from (5'α,17'β)-13'-ethyl-4,5-dihydro-11'-methylenespiro[furan-2(3 H),17'-qon-3-ene]-3-one. M.p. 136.8° C. $[\alpha]_D^{20}$=+8.50° (c=1.02, chloro- form).

(17α)-17,23-epoxy-11-methylene-19,24-dinorchola-4,20-diene from (17α)-4',5'-dihydro-11-methylenespiro[estr-4-ene-17,2'(3' H)-furan]-3'-one. M.p. 106.6° C. $[\alpha]_D^{20}$=+29.9° (c=1.0, chloroform).

(3'E,17β)-3'-ethylidene-4',5'-dihydro-11-methylene-spiro [estr-4-ene-1 7,2'(3' H)-furan] from (17β)-4',5'-dihydro-11-methylenespiro[estr-4-ene-17,2'(3' H)-furan]-3'-one and eth-yltrimethylphosphonium bromide. M.p. 139.8° C. $[\alpha]_D^{20}$=+38.8° (c=1.0, chloroform).

EXAMPLE 5

E-[(17β)-4',5'-dihydro-3-oxospiro[estr-4-ene-17,2'(3'H)-furan]-3'-ylidene]acetonitrile was obtained as follows:

(i) To a suspension cf 1.2 g of lithium diisopropylamide in 30 ml of toluene 0.58 ml of acetonitrile were added at −40° C. The mixture was then stirred at −20° C. for 20 minutes, cooled to −50° C., and 358 mg of (17β)-3-ethoxy-4',5'-dihydrospiro[estra-3,5-diene-17,2'(3'H)-furan]-3'-one were added. The mixture was allowed to warm to −10° C., and after 20 min poured into a saturated ammonium chloride solution. The organic layer was separated, washed with brine, dried over magnesium sulfate, and concentrated under reduced pressure. The residue was taken up in a mixture of 5 ml of acetone and 3 ml of 0.1N hydrochloric acid, stirred at room temperature for 2 h, and then partitioned between water and ethyl acetate. The organic layer was dried over magnesium sulfate and concentrated under reduced pressure. Chromatography of the residue afforded 200 mg (54%) of (3'S,17β)-4',5'-dihydro-3'-hydroxy-3-oxospiro[estr-4-ene-17,2'(3' H)-furan]-3'-acetonitrile.

(ii) 200 mg of the above-mentioned nitrile were dissolved in 10 ml of dry pyridine, and 0.07 ml of phosphorus oxychloride were added. The reaction mixture was refluxed for 30 min, cooled, and then poured into ice-water. The mixture was acidified with 2N hydrochloric acid and extracted with ethyl acetate. The extract was washed with water and with brine, dried over magnesium sulfate, and concentrated under reduced pressure. The residue was chromato-graphed to afford 90 mg (47%) of E-[(17β)-4',5'-dihydro-3-oxospiro[estr-4-ene-17,2'(3' H)-furan]-3'-ylidene] acetonitrile. M.p. 193.5° C.

EXAMPLE 6

(17α)-17,23-epoxy-19,24-dinorchola-5(10),20-dien-3-one was prepared from the known (17β)-3-methoxyspiro[estra-1,3,5(10)-triene-17,2'(3' H)-furan]-3'-one (see D. Gange and Ph. Magnus, J. Am. Chem. Soc. 100, 7746–7747 (1978)) as follows:

(i) The above-mentioned trienone was converted to (17α)-3-methoxy-17,23-epoxy-19,24-dinorchola-1,3,5(10),20-tetraene as described for Example 1

(ii) 5 g of the tetraene were then dissolved in 350 ml of tetrahydrofuran and this solution added to a solution of 4.3 g of lithium dissolved in 430 ml of ammonia which was maintained at −33° C. After 4 h at this temperature 50 ml of ethanol were slowly added and the ammonia allowed to evaporate. The residue was partitioned between water and dichloromethane, the organic layer washed with water, dried over magnesium sulfate and concentrated under reduced pressure, affording after recrystallization from ethanol 2.12 g of (17α)-3-methoxy-17,23-epoxy-19,24-dinorchola-2,5(10),20-triene.

(iii) 2.12 g of the above-mentioned triene were suspended in 155 ml of methanol to which suspension was added a solution of 2.33 g of oxalic acid in 30 ml of water. The mixture was stirred overnight at ambient temperature, after which diethyl ether was added. The ethereal layer was separated and washed three times with a saturated solution of sodium bicarbonate and once with water, dried over magnesium sulfate, and concentrated under reduced pressure. The residue was chromatographed to afford 0.7 g of the desired dienone as an amorphous solid. $[\alpha]_D^{20}$=+84° (c=0.935, chloroform).

EXAMPLE 7

(17α)-17,23-epoxy-19,24-dinorchola-4,20-dien-3-one oxime was prepared from (17α)-17,23-epoxy-19,24-dinorchola-4,20-dien-3-one as follows: a mixture of 0.7 g of hydroxylamine hydrochloride, 0.56 g of potassium hydroxide and 0.44 g of the starting ketone in 50 ml of ethanol was refluxed overnight. Subsequently, the solvent was removed under reduced pressure and the residue partitioned between water and dichloromethane. The organic layer was dried over sodium sulfate and concentrated under reduced pressure to afford after recrystallization from diisopropyl ether 0.23 g of a 3:1 mixture of the E and Z oxime. M.p. 269.5° C. $[\alpha]_D^{20}$=+43.6° (c=0.975, chloroform).

EXAMPLE 8

(3α,17α)-17,23-epoxy-19,24-dinorchola-4,20-dien-3-ol was prepared from (17α)-17,23-epoxy-19,24-dinorchola-4,20-dien-3-one as follows: 0.65 g of the ketone were dissolved in 10 ml of methanol under a nitrogen atmosphere. 80 mg of sodium borohydride were added and the mixture was stirred at ambient temperature for 1.5 h. The reaction mixture was then partitioned between water and dichloromethane. The organic layer was washed with 0.1N hydrochloric acid and with brine, and dried over sodium sulfate. Removal of the solvent under reduced pressure afforded 0.62 g of crude material, from which the above alcohol could be obtained by crystallization from ethyl acetate. M.p. 132.3° C. $[\alpha]_D^{20}$=−58.9° (c=1.36, chloroform). Column chromatography of the mother liquor of the above reaction afforded (3α,17α)-17,23-epoxy-19,24-dinorchola-4,20-dien-3-ol as an amorphous solid. $[\alpha]_D^{20}$=+11.0° (c =1.14, chloroform).

EXAMPLE 9

(3β,17α)-17,23-epoxy-9,24-dinorchola-4,20-dien-3-ol acetate (ester) was prepared from (3β,17α)-17,23-epoxy-19,24-dinorchola-4,20-dien-3-ol, mentioned above, as follows: 0.81 g of the alcohol were dissolved in 4 ml of pyridine and 1 ml of acetic anhydride was added. The mixture was stirred overnight under a nitrogen atmosphere and then coevaporated three times with toluene; the residue was partitioned between water and dichloromethane; the latter was dried over sodium sulfate and concentrated under reduced pressure. The residue was recrystallized from ethyl acetate to afford 0.55 g of the ester. M.p. 177.7° C. $[\alpha]_D^{20}$=−96.6° (c=1.02, chloroform).

EXAMPLE 10

Alternatively, the compounds described in Examples 1–9 can be prepared as follows: The conversion of e.g. (17β)-3-ethoxy-4',5'-dihydrospiro[androsta-3,5-diene-17,2'(3' H)-furan]-3'-one to (17α)-17,23-epoxy-24-norchola-4,20-dien-3-one could be effected by treatment of the former with trimethylsilylmethylmagnesium chloride, followed by acid treatment, which not only produces the desired olefin but also effects hydrolysis of the acid-labile protecting group. For the selective transformation of the 3'-carbonyl group, the ketone at C-3 of the steroid ring, if present, can also be protected with other protecting groups known in the art, e.g. an acetal or a thioketal. Moreover, (17α)-17,23-epoxy-3-ethoxy-24-norchola-3,5,20-triene could be prepared directly by treatment of 3-ethoxyandrosta-3,5-dien-17-one with 4-chloro-2-lithio-1-butene (see e.g. E. Piers and V. Karunaratne, Tetrahedron 45, 1089–1104 (1989)). Finally, introduction of the 20–21 double bond into the cholane system could also be effected by an elimination reaction of an (17α,20ε)-17,23-epoxy-24-norcholane precursor possessing a suitable leaving group in either the 20- or the 21-position.

EXAMPLE 11 a. To a solution of 25.6 g of (17β)-4',5'-dihydro-3-methoxyspiro[estra-1,3,5(10)-triene-17,2'(3' H) -furan]-3'-one (see D. Gange and Ph. Magnus, J. Am. Chem. Soc., 100 (1978), 7746–7747) in 200 ml of ethanol and 200 ml of toluene were added 2.85 g of sodium borohydride and the mixture was stirred at room temperature for 16 h. Acetic acid was added until pH 7, followed by addition of water, and the mixture was extracted with toluene. Removal of the solvent under reduced pressure afforded the crude alcohol, which was crystallized from methanol to yield 24 g of (17β3'S)-4',5'-dihydro-3-methoxy-spiro[estra-1,3,5(10)-triene-17, 2',(3' H)-furan]-3'-ol. M.p. 130° C.

b. (i) A solution of 9 g of (17β,3'S)-4',5'-dihydro-3-methoxyspiro[estra-1,3,5(10)-triene-17,2'(3' H) -furan]-3'-ol in 150 ml of tetrabydrofuran was added to a solution of 4 g of lithium in 450 ml of liquid ammonia at −33° C. After stirring for 3 h at this temperature 60 ml of ethanol were added and the ammonia was allowed to evaporate. The residue was partitioned between water and ethyl acetate. The organic layer was washed with brine, dried over magnesium sulfate and concentrated under reduced pressure, affording after trituration with diisopropyl ether 8.9 g of (17β,3'S)-4', 5¹-dihydro-3-methoxyspiro[estra-2,5(10)-diene-17,2¹(3' H) -furan]-3'-ol.

(ii) 80.9 g of the above-mentioned diene were dissolved in 65 ml of methanol and 65 ml of tetrahydrofuran. At 5° C. a solution of 4.6 g of oxalic acid in 45 ml of water and 22 ml of methanol was added. After stirring for 6 h at ambient temperature the mixture was poured into an ice-cold 1% sodium hydrogen carbonate solution and extracted with ethyl acetate. The organic layer was washed with brine, dried over magnesium sulfate and concentrated under reduced pressure to give 8.5 g of the crude (17β,3'S)-4',5'-dihydro-3'-hydroxyspiro[estr-5 (10)-ene-17,2'(3' H)-furan]-3-one.

(iii) 8.5 g of this ketone were dissolved in 90 ml of pyridine. To this solution were added portionwise 10 g of phenyltrimethylammonium tribromide during 15 min at 0° C. After stirring for 3 h at room temperature the mixture was poured into 800 ml of ice-water and the product extracted with ethyl acetate. The organic layer was washed with 2M hydrochloric acid and with brine, and dried over magnesium sulfate. The residue was chromatographed after evaporation of the solvent to yield 4.7 g of (17β,3'S)-4',5'-dihydro-3'-hydroxyspiro [estra-4,9-diene-17,2'(3' H)-furan]-3-one. M.p. 180° C.

c. (i) A mixture of 4.1 g of (17β,3'S)-4',5'-dihydro-3'-hydroxyspiro[estra-4,9-diene-17,2'(3' H)-furan]-3-one, 30 ml of dichloromethane, 30 ml of ethylene glycol, 10 ml of triethyl orthoformate and 200 mg para-toluenesulphonic acid was stirred for 2 h at room temperature. The reaction was stopped by the addition of water and sodium hydrogen carbonate, the layers were separated and the organic layer was washed with water. After drying over magnesium sulfate and concentration under reduced pressure 5.1 g of the crude (17β,3'S)-4',5'-dihydro-3'-hydroxyspiro[estra-4,9-diene-17,2'(3' H)-furan]-3-one cyclic 1,2-ethanediyl acetal were obtained, which was used in the next step without further purification.

(ii) A mixture of 5.1 g of the above-mentioned compound, 200 ml of toluene, 36 ml of cyclohexanone and 3.6 g of aluminum iso-propoxide was refluxed for 3 h. After cooling to room temperature, ethyl acetate was added and the mixture was washed repeatedly with a 75% w/v solution of Seignette salt. The organic layer was washed with water and brine, and dried over magnesium sulfate. Evaporation of the solvent under reduced pressure followed by chromatography afforded 4 g of (17β) -4',5'-dihydrospiro[estra-5(10),9(11)-diene- 17,2' (3' H)-furan]-3,3'-dione cyclic 3-(1,2-ethane-diyl acetal). M.p. 146° C.

d. To a suspension of 3.09 g of methyltriphenyl-phosphonium bromide in 25 ml of toluene were added 0.83 g of potassium tert-butoxide. The mixture was refluxed for 45 min, and then cooled, after which a solution of 1.10 g of the acetal of c(ii) in 2 ml of toluene were added and the mixture was refluxed for 1 hour. The suspension was subsequently poured into ice-water, the toluene layer separated, washed with brine, dried over magnesium sulfate and concentrated under reduced pressure. The residue was chromato-graphed to afford 0.95 g of (17α)-17,23-epoxy-19,24-dinorchola-5(10),9(11),20-trien-3-one cyclic 1,2-ethanediyl acetal. M.p. 132° C.

e. (i) To a solution of 3.7 g of the acetal of d in 25 ml of dichloromethane were added 5 g of sodium hydrogen carbonate. To this mixture were added at −40° C. a solution of 2.5 g of meta-chloroperbenzoic acid in 15 ml of dichloromethane. After stirring for 30 min at 0° C., the mixture was poured into ice-water and extracted with dichloromethane. The organic layer was washed with a sodium hydrogen carbonate solution and with water, dried over magnesium sulfate and concentrated under reduced pressure. The residue was chromatographed to give 1.8 g of the intermediate 5α,10α-epoxide. Alternatively, the intermediate 5α,10α-epoxide can be prepared using 30% $H_2O_2$/PhC(O)$CF_3$ as described in German Patent DE 3722486.

(ii) To a solution of [4-(N,N-dimethylamino)phenyl]-magnesium bromide (prepared from 4.4 g of 4-bromo-N,N-dimethylaniline and 0.6 g of magnesium) in 40 ml of tetrahydrofuran were added 0.5 g of copper-(I) chloride at room temperature. Subsequently, 1.8 g of the 5α,10α-epoxide of e(i) in 10 ml of tetra-hydrofuran were added and stirring was continued for 30 min. The mixture was poured into an ammonium chloride solution and extracted with ethyl acetate. After washing with water, the organic layer was dried over magnesium sulfate and concentrated under reduced pressure. The residue was chromatographed to afford 1.4 g of the intermediate (5α,11β,17α) -11-[(4-dimethylamino) phenyl]-17,23-epoxy-5-hydroxy-19,24-dinorchola-9, 20-dien-3-one cyclic 1,2-ethane-diyl acetal.

(iii) 1.4 g of the acetal of e(ii) in 15 ml of 70% acetic acid were heated for 2 h at 50° C. After cooling to room temperature the mixture was neutralized with sodium hydrogen carbonate and extracted with ethyl acetate. After drying over magnesium sulfate, the solvent was evaporated and the residue chromatographed to give 0.9 g of (11β,17α)-11-[(4-dimethylamino)phenyl]-17, 23-epoxy-19,24-dlnorchola-4,9,20-trien-3-one. M.p. 168° C.; $[\alpha]_D^{20}$=+125° (c=1.135, dioxane).

EXAMPLE 12

In an analogous manner as described in Example 11 were prepared:

(11β,17α)-17,23-epoxy-11-(4-ethenylphenyl)-19,24-dinorchola-4,9,20-trien-3-one. M.p. 191° C; $[\alpha]_D^{20}$=+128° (c =0.94, dioxane).

(11β,17α)-11-(4-acetylphenyl)-17,23-epoxy-19,24-dinorchola-4,9,20-trien-3-one. M.p. 126° C; $[\alpha]_D^{20}$=+82° (c =0.955, dioxane).

(11β,17α)-17,23-epoxy-11-(4-methoxyphenyl)-19,24-dinorchola-4,9,20-trien-3-one. M.p. 185° C.

(11β,17α) -17,23-epoxy-11- (4-methylthiophenyl) -19, 24-dinorchola-4,9,20-trien-3-one. M.p. 186° C; $[\alpha]_D^{20}$=+121° (c=1.155, dioxane).

(7β,11β,17α)-11-[(4-dimethylamino)phenyl]-17,23-epoxy-7-methyl-19,24-dinorchola-4,9,20-trien-3-one. M.p. 100° C; $[\alpha]_D^{20}$=+368° (c=1.02, dioxane).

(6β,11β,17α)-11-[(4-dimethylamino)phenyl]-17,23-epoxy-6-methyl-19,24-dinorchola-4,9,20-trien-3-one. M.p. 89° C; $[\alpha]_D^{20}$=+128° (c=1.03, dioxane).

4-[(11β,17α)-17,23-epoxy-3-oxo-19,24-dinorchola-4,9, 20-trien-11-yl]benzaldehyde. M.p. 187° C.

(11β,17α)-17,23-epoxy-11-[4-(4,5-dihydro-4,4-dimethyl-2-oxa-zolyl)phenyl]-19,24-dinorchola-4,9,20-trien-3-one. M.p. 240° C.

4-[(11β,17α)-17,23-epoxy-3-oxo-19,24-dinorchola-4,9, 20-trien-11-yl]-N-(2-hydroxy-1,1-dimethylethyl) benzamide, m.p. 170° C., was obtained after continued exposure of the above-mentioned 2-oxazolylphenyl compound to 70% acetic acid at 50° C.

The E and Z-ethylidene derivatives were prepared analogously to the preparation of (11β,17α)-11-[(4-dimethylamino)phenyl]-17,23-epoxy-19,24-dinorchola-4,9,20-trien-3-one by using ethyl triphenylphosphonium bromide. Separation by chromatography afforded: (3'E,11β, 17β)-11-[(4-dimethylamino)phenyl]-3'-ethylidene-4',5'-dihydrospiro[estra-4,9-diene-17,2'(3' H) -furan]-3-one, M.p. 175° C; $[\alpha]_D^{20}$=+128° (c=0.885, dioxane), and (3'Z,11β, 17β)-11-[(4-dimethylamino) -phenyl]-3'-ethylidene-4',5'-dihydrospiro[estra-4,9-diene-17,2'(3' H)-furan]-3-one, M.p. 172° C.

(11β,17α)-17,23-epoxy-11-ethenyl-19,24-dinorchola-4, 9,20-trien-3-one was prepared from (17α)-17,23-epoxy-19, 24]dinorchola-5(10),9(11),20-trien-3-one cyclic 1,2-ethanediyl acetal. The resulting compound was a gum.

(11β,17α)-17,23-epoxy-11-[4-(1-hydroxyethyl)phenyl]-19,24-dinorchola-4,9,20-trien-3-one. The product was an inseparable 1:1 epimer mixture. M.p. 200° C.

(11β,17α)-17,23-epoxy-11-(4-hydroxyphenyl)-19,24-dinorchola-4,9,20-trien-3-one. $[\alpha]_D^{20}$=+58° (c=0.5, dichloromethane).

EXAMPLE 13

A solution of 870 mg of 4-[(11β,17α)-17,23-epoxy-3-oxo-19,24-dinorchola-4 9,20-trien-11-yl]benzaldehyde (Example 12) and 142 mg of hydroxylamine hydrochloride in 20 ml of pyridine was stirred for 16 h at room temperature. After evaporation of the solvent the residue was chromatographed to afford 750 mg of an E/Z-isomer mixture of 4-[(11β,17α)-17,23-epoxy-3-oxo-19,24-dinorchola-4,9,20-trien-11-yl]benzaldehyde oxime. M.p. 250° C.

EXAMPLE 14

300 mg of the E/Z-isomer mixture of the oximes of Example 13 were heated in 6 ml of acetic anhydride for 2 h. After removal of the solvent under reduced pressure, the residue was chromatographed to give 230 mg of 4-[(11β, 17α)-17,23-epoxy-3-oxo-19,24-dinorchola-4,9,20-trien-11-yl]benzonitrile. M.p. 218° C. 10 Example 15

A mixture of 350 mg of (11β,17α)-11-[(4-dimethylamino) -phenyl]-17,23-epoxy-19,24-dinorchola-4,9,20-trien-3-one (Example 11) and 57 mg of hydroxylamine hydrochloride in 6 ml of pyridine was heated at 90° C. for 30 min. After cooling to room temperature, the mixture was poured into water, filtered, and dried to give 300 mg of a 2/1 mixture of (3E/Z,11β,17α)-11-[(4-dimethylamino)phenyl]-17,23-epoxy-19,24-dinorchola-4,9,20-trien-3-one oxime. M.p. 148° C; $[\alpha]_D^{20}$=+145° (c=1.22, dioxane).

EXAMPLE 16 a. A mixture of 520 mg of (5α,11β,17α)-17,23-epoxy-5-hydroxy-11-[(4-methylthio)phenyl]-19,24-dinorchola-9,20-dien-3-one cyclic 1,2-ethanediyl acetal [prepared analogously to Example 11e(ii)], 5 ml of acetone and 0.1 ml of 30% hydrogen peroxide was refluxed for 2 h. After cooling to room temperature, water was added and the mixture was extracted with ethyl acetate. The organic layer was washed with a sodium thiosulfate solution and with water, dried over magnesium sulfate and concentrated under reduced pressure.

b. The residue of the above step (515 mg) was dissolved in 5 ml of 70% acetic acid and heated for 3 h at 50° C. After cooling to room temperature the mixture was neutralized with sodium hydrogen carbonate and extracted with ethyl acetate. After drying over magnesium sulfate, the solution was filtered over silica gel to give 250 mg of a mixture of diastereomeric sulfoxides of (11β,17α)-17,23-epoxy-11-[4-(methylsulfinyl)phenyl]-19,24-dinorchola-4,9,20- trien-3-one. Although possible, the diastereomers were not separated by chromatography. M.p. 115° C.

EXAMPLE 17

670 mg of (11β,17α)-11-[(4-dimethylamino)phenyl]-17, 23-epoxy-19,24-dinorchola-4,9,20-trien-3-one (Example 11) were dissolved in 45 ml of ethanol under a nitrogen atmosphere. 210 mg of sodium borohydride were added and the mixture was stirred at ambient temperature for 3 h. Water was added and acetic acid until pH 7 and the mixture was extracted with ethyl acetate. The organic layer was dried over magnesium sulfate and concentrated under reduced pressure. The residue was chromatographed to give (3β,11β, 17α)-11-[(4-dimethylamino)phenyl]-17,23-epoxy-19,24-dinorchola-4,9,20-trien-3-ol. M.p. 95° C; $[\alpha]_D^{20}$=+102° (c=0.525, dioxane) and (3α,11β,17α)-11-[(4-dimethylamino)phenyl]-17,23-epoxy-19,24-dinorchola-4,9, 20-trien-3-ol. M.p. 110° C; $[\alpha]_D^{20}$=+16° (c=0.5, dioxane).

EXAMPLE 18 a. To a solution of 520 mg of a diastereomeric mixture of (5α,11β,17α)-17,23-epoxy-5-hydroxy-11-[4-(methylsulfinyl)phenyl]-19,24-dinorchola-9,20-dien-3-one cyclic 1,2-ethanediyl acetal (Example 16a) in 5 ml of methyl alcohol was added, at 5° C., a solution of 615 mg of oxone in 6 ml of water. After stirring for 3 h at this temperature the mixture was extracted with dichloromethane. The organic layer was washed with water, dried over magnesium sulfate and concentrated under reduced pressure.

b. The residue (520 mg) of step a) was dissolved in 5 ml of 70% acetic acid and heated for 3 h at 50° C. After cooling to room temperature the mixture was neutralized with sodium hydrogen carbonate and extracted with ethyl acetate. After drying over magnesium sulfate, the solvent was removed and the residue was chromatographed to give 510 mg of (11β,17α)-17,23-epoxy-11-[4-(methylsulfonyl) phenyl]-19,24-dinorchola-4,9,20-trien-3-one. M.p. 142° C.

EXAMPLE 19

138 mg of the 3β-alcohol (Example 17) were dissolved in 0.5 ml of pyridine and 0.25 ml of acetic anhydride was added. The mixture was stirred overnight under a nitrogen atmosphere, poured into water and extracted with ethyl acetate. The organic layer was dried over magnesium sulface, concentrated under reduced pressure and chromatographed to afford 100 mg of (3β,11β,17α)-11-[(4-dimethylamino)phenyl]-17,23-epoxy-19,24-dinorchola-4,9, 20-trien-3-ol acetate (ester). M.p. 148° C.

EXAMPLE 20 a. A solution of 5 g of the epoxide of Example 11e in 15 ml of tetrahydrofuran was added at 0° C. to a suspension of (2-bromo-5-methoxybenzyl)magnesium chloride (prepared from 1.15 g of magnesium and 12.4 g of 2-bromo-5-methoxybenzylchloride) in 42 ml of diethyl ether. The mixture was stirred overnight at room temperature. Work-up as described in Example 11e afforded after chromatography 4.3 g of (17α)-19-[1-(2-bromo-5-methoxy)phenyl]-17,23-epoxy-5-hydroxy-24-norchol-9(11)-en-3-one cyclic 1,2-ethanediyl acetal.

b. A mixture of 1 g of this acetal, 0.74 ml of tri-n-butyltin hydride, 83 mg of 2,2'-azobis(2-methyl-propionitrile) in 83 ml of toluene was refluxed for 3 h. After cooling to room temperature, 25 ml of a saturated potassium fluoride solution was added and stirring was continued for 1 h. The layers were separated, the water layer extracted with ethyl acetate, and the combined organic layers were washed with water and brine. After drying over magnesium sulfate and evaporation of the solvent, the residue was chromatographed to give 0.71 g of the intermediate (5α,11α,17α)-17,23-epoxy-9,11-dihydro-5-hydroxy-6'-methoxy-4' H-naphtho[3',2',1':10,9,11]-19,24-dinorchol-9(11),20-dien-3-one cyclic 1,2-ethanediyl acetal. M.p. 226° C.

c. A solution of 0.7 g of this acetal in 50 ml of acetone and 2.5 ml of 4M hydrochloric acid was stirred at 40° C. for 45 min. After cooling to room temperature, sodium hydrogen carbonate was added and the mixture was extracted with ethyl acetate. The organic layer was dried over magnesium sulfate, the solvent removed in vacuo and the residue was chromatographed to give 0.4 g of (11β,17α)-17,23-epoxy-9,10-dihydro-6'-methoxy-4' H-naphtho [3',2',1': -10,9,11]-19,24-dinorchola-4,9(11),20-trien-3-one. M.p. 206° C.

EXAMPLE 21

The intermediate of Example 11d can also be prepared by treatment of (17β)-4',5'-dihydrospiro[estra-5(10),9(11)-diene-17,2'(3' H)-furan]-3,3'-dione cyclic 3-(1,2-ethanediyl acetal) with trimethylsilylmethylmagnesium chloride, followed by acid treatment.

EXAMPLE 22 a. In an analogous manner as described in Example 20a, 1.1 g of (17α)-17,23-epoxy-5-hydroxy-19-(3-methoxyphenyl)-24-norchola-9(11),20-dien-3-one cyclic 1,2-ethanediyl acetal were prepared. M.p. 164° C.

b. A solution of 1.1 g of the above-mentioned acetal in 50 ml of acetone containing 2.5 ml of 4M hydrochloric acid was stirred for 2 h at 40° C. Work up as described in Example 20c afforded, after chromatography, 0.7 g of (17α)-17,23-epoxy-19-(3-methoxyphenyl)-24-norchola-4,9(11),20-trien-3-one. M.p. 169° C.

EXAMPLE 23

The intermediate of Example 11c(ii) can also be prepared by converting the known estra-5(10),9(11)-diene-3,17-dione cyclic 3-(1,2-ethanediyl acetal) (A. Belanger, D. Philibert, and G. Teutsch, Steroids 37 (1981), 361–383) in a similar manner as described by D. Gange and Ph. Magnus, J. Am. Chem. Soc. 100 (1978), 7747–7748:

(i) To 65 ml of n-butyllithium (1.6M solution in hexane) in 48 ml of tetrahydrofuran were added at −78° C. 9.3 ml of 1-methoxy-1,2-propadiene. After stirring for 45 min at this temperature 10.6 g of estra-5(10),9(11)-diene-3,17-dione cyclic 3-(1,2-ethanediyl acetal) were added. Subsequently, the mixture was stirred at −40° C. for 30 min and poured into an ice-cold ammonium chloride solution. Ethyl acetate was added and the layers were separated. The organic layer was washed with brine and dried over magnesium sulfate, and the solvent was removed under reduced pressure.

(ii) The crude 1,2-propadiene was mixed with 230 ml of tert-butanol, 3.75 g of potassium tert-butoxide and 0.3 g of dicyclohexano-18-crown-6. After refluxing for 8 h, the mixture was poured into water and extracted with ethyl acetate. The organic layer was dried over magnesium sulfate, evaporated, and the residue was chromatographed to afford 9.1 g of (17β) -3'-methoxyspiro[estra-5(10),9(11)-diene-17,2'(5' H) -furan]-3-one cyclic 1,2-ethanediyl acetal.

(iii) This enol ether was dissolved in 70 ml of acetone and a 1M hydrochloric acid solution was added until pH 2. The mixture was stirred for 3 h, subsequently poured into a sodium hydrogen carbonate solution, and extracted with ethyl acetate. After drying over magnesium sulfate and removal of the solvent, the residue was subjected to chromatography to yield 6.4 g of (17β)-4',5'-dihydro-spiro[estra-5(10),9(11) -diene-17,2'(3' H)-furan]-3,3'-dione cyclic 3-(1,2-ethanediyl acetal).

EXAMPLE 24 a. To a solution of 1.2 g of (17α)-19-[1-(2-bromo-5-methoxy)phenyl]-17,23-epoxy-5-hydroxy-24-norchola-9(11),20-dien-3-one cyclic 1,2-ethanediyl acetal (Example 20a) in 17 ml of dichloromethane were added a solution of 123 mg of sodium hydrogen carbonate in 4.6 ml of water and 400 mg of m-chloroperbenzoic acid. After stirring for 1.5 h the mixture was worked up as described in Example 11e(i). Chromatography gave 880 mg of the intermediate 9β,11β-epoxide.

b. A mixture of 880 mg of this epoxide, methylmagnesium iodide (prepared from 220 mg of magnesium and 0.9 ml of methyl iodide in 9 ml of diethyl ether) and 17.5 ml of n-butyllithium (1.6M solution in hexane) was stirred for 16 h at room temperature. Work up as described in Example 11e(ii) afforded the crude 9-hydroxy 3-acetal derivative, which was dissolved in 50 ml of acetone containing 2.5 ml of 4M hydrochloric acid. After stirring for 45 min at 40° C. the mixture was worked up as described in Example 20c to yield after purification by chromatography 50 mg of (9α,11α,17α)-17,23-epoxy-9,11-dihydro-9-hydroxy-6'-methoxy-4' H-naphtho[3',2',1':10,9,11]-19,24- dinorchola-4,9(11),20-trien-3-one. $[\alpha]_D^{20}$=−6° (c 1.0, dioxane).

EXAMPLE 25

The intermediate of Example 11d can also be prepared in one step by a reaction of estra-5(10),9(11)-dien-3,17-dione cyclic 3-(1,2-ethanediyl acetal) with 4-chloro-2-lithio-1-butene.

EXAMPLE 26 a. To a solution of 1.5 ml of 1-methoxy-1,2-propadiene in 21 ml of tetrahydrofuran were added 10.2 ml of n-butyllithium (1.6M solution in hexane) at -78° C. After stirring for 45 min, 2.2 g of (11β)-11-(4-methoxyphenyl)-estr-5-en-3,17-dione cyclic 3-(1,2-ethanediyl acetal) (described in German patent application DE 4018167) were added and stirring was continued for 1 h at −78° C. and 45 min at −30° C. The mixture was poured into water, ethyl acetate was added and the layers were separated. The organic layer was washed with brine, dried over magnesium sulfate, and the solvent was removed under reduced pressure.

b. This crude 1,2-propadiene was mixed with 75 ml of tert-butanol, 0.65 g of potassium tert-butoxide and 0.3 g of dicyclohexano-18-crown-6. After refluxing for 16 h, the mixture was poured into water and extracted with ethyl acetate. The organic layer was dried over magnesium sulfate, evaporated, and the residue was chromatographed to afford 2.5 g of (11β,17β)-3'-methoxy-11-(4-methoxyphenyl) spiro-[estr[5]ene-17,2'(5' H)-furan]-3-one cyclic 1,2 -ethanediyl acetal.

c. To a stirred suspension of 7.5 g of silica gel and 0.75 ml of a saturated aqueous oxalic acid solution in 15 ml of dichloromethane were added 2.5 g of the above-mentioned methyl enolether. After stirring for 1 h at room temperature the mixture was filtered and the silica gel was washed with dichloromethane containing 5% of methanol. The filtrate was washed with a sodium hydrogen carbonate solution and with water and dried over magnesium sulfate. Chromatography afforded 2.1 g of (11β,17β)-4',5'-dihydro-11-(4-methoxyphenyl)spiro[estr[5]ene-17,2'-(3' H)-furan]-3,3'-dione cyclic 3-(1,2-ethanediyl acetal). M.p. 175° C.

d. To a suspension of 1.6 g of methyltriphenylphosphonium bromide in 15 ml of toluene were added 0.43 g of potassium tert-butoxide. The mixture was refluxed for 45 min, cooled to room temperature, after which a solution of 1.4 g of the above-mentioned acetal (Example 26c) in 10 ml of toluene were added and the mixture was refluxed for 45 min. The suspension was poured into ice water, the toluene layer separated, washed with brine, dried over magnesium sulfate and concentrated under reduced pressure. The residue was chromatographed to yield 1 g of (11β,17α)-17,23-epoxy-11-(4-methoxyphenyl)-19,24-dinorchola-5,20-dien-3-one cyclic 1,2-ethanediyl acetal. M.p. 179° C.

e. A mixture of 1 g of the above-mentioned acetal, 50 ml of acetone and 2.5 ml of 4M hydrochloric acid was stirred for 2 h at 40° C. After cooling to room temperature, the mixture was neutralized with sodium hydrogen carbonate and extracted with ethyl acetate. After drying over magnesium sulfate and concentration, chromatography afforded 0.8 g of (11β,17α)-17,23-epoxy-11-(4-methoxyphenyl)-19,24-dinorchola-4,20-dien-3-one. M.p. 185.5° C.

EXAMPLE 27

In an analogous manner as described in Example 26 were prepared: (11β,17α)-11-[4-(dimethylamino)phenyl]-17,23-epoxy-19,24-dinorchola-4,20-dien-3-one from (11β)-11-[4-(dimethylamino)phenyl]-estr-5-ene-3,17-dione cyclic 3-(1,2-ethanediyl acetal). $[\alpha]_D^{20}$=+25° (c=1.025,dioxane).

(11β,17α)-17,23-epoxy-11-(4-methoxyphenyl)-19,24-dinorchola-4,15,20-trien-3-one from (11β)-11-(4-methoxyphenyl)-estra-5,15-diene-3,17-dione cyclic 3-(1,2-ethanediyl acetal) (DE 4042004). M.p. 166° C.

(11β,17β,3'E)-3'-ethylidene-4',5'-dihydro-11-(4-methoxyphenyl)spiro[estr-4-ene-17,2'(3' H)-furan]-3-one (M.p. 184° C.) and (11β,17β,3'Z)-3'-ethylidene-4',5'-dihydro-11-(4-methoxyphenyl)spiro[estr-4-ene-17,2'(3' H)-furan]-3-one (M.p. 174° C.) from (11,17β)-4',5'-dihydro-11-(4-methoxyphenyl)spiro[estr-5-ene-17,2'(3' H)-furan]-3,3'-dione cyclic 3-(1,2-ethanediyl acetal) (Example 26c) by treatment with ethyl triphenylphosphonium iodide, followed by separation by chromatography.

EXAMPLE 28 a. A mixture of 1.4 g of the acetal of Example 26d, 0.84 g of sodium thiomethoxide and 10 ml of N,N-dimethylformamide was refluxed for 3 h. Work-up as described in Example 11e afforded after chromatography 1 g of (11β,17α)-17,23-epoxy-11-(4-hydroxyphenyl)-19,24-dinorchola-5,20-dien-3-one cyclic 1,2-ethanediyl acetal. M.p. 222° C.

b. A solution of 1 g of this acetal in 50 ml of acetone and 2.5 ml of 4M hydrochloric acid was stirred for 2 h at 40° C. After cooling sodium hydrogen carbonate was added and the mixture was extracted with ethyl acetate. The organic layer was dried over magnesium sulfate, concentrated, and the residue was chromato-graphed to afford 0.75 g of (11β,17α)-17,23-epoxy-11-(4-hydroxyphenyl)-19,24-dinorchola-4,20-dien-3-one. M.p. 149° C.

EXAMPLE 29 a. To a solution of 5.46 g of the acetal of Example 28a and 2.1 ml of triethylamine in 120 ml of dichloro-methane were added 2.3 ml of trifluoromethanesulfonic anhydride at 0° C. After 30 min stirring at this temperature the mixture was poured into a sodium hydrogen carbonate solution, the layers were separated, and the organic layer was washed with water and brine. Drying over magnesium sulfate, evaporation of the solvent and chromatography yielded 6.8 g of 4-[(11β,17α)-17,23-epoxy-3,3-[1,2-ethanediylbis(oxy)]-19,24-dinorchola-5,20-dien-11-yl]phenol trifluoromethanesulfonate. M.p. 198° C.

b. A suspension of 2.2 g of the triflate obtained above and 0.3 g of lithium chloride in 28 ml of N,N-dimethylformamide was stirred for 15 min at room temperature. Subsequently, 0.22 g of tetrakis-(triphenylphosphine)palladium(0) and 1.3 ml of (1-ethoxyvinyl)tributyltin were added and the mixture was refluxed for 3 h. After cooling, the suspension was diluted with ethyl acetate and filtered over celite, which was washed thoroughly with ethyl acetate. The filtrate was treated with brine, and dried over magnesium sulfate. Removal of the solvent gave 1.4 g of the crude acetal, which was used in the next step without further purification.

c. A mixture of 1.4 g of the above-mentioned acetal, 70 ml of acetone and 3.5 ml of 4M hydrochloric acid was stirred for 2 h at 40° C. Work-up as described in Example 11e gave, after chromatography, 1 g of (11β,17α)-11-(4-acetylphenyl)-17,23-epoxy-19,24-dinorchola-4,20-dien-3-one. M.p. 223° C.

EXAMPLE 30 a. A suspension of 2.2 g of the triflate of Example 29a and 0.48 g of lithium chloride in 75 ml of dioxane was stirred for 15 min at room temperature. Subsequently, 0.22 g of tetrakis (triphenyl-phosphine)palladium(o) and 5.6 ml of bis (tributyl)tin were added and the mixture was refluxed for 2 h. After cooling, 6.75 g of 4-bromobenzonitrile were added and refluxing was continued for 24 h. The mixture was poured into brine and ethyl acetate was added. The organic layer was separated, dried over magnesium sulfate and evaporated. The residue was purified by chromatography to afford 1.3 g of 4'-[(11β,17α)-17,23-epoxy-3,3-[1,2-ethanediylbis(oxy)]-19,24-dinorchola-5,20-dien-11-yl]-1,1'-biphenyl-4-carbonitrile.

b. A mixture of 1.3 g of the above-mentioned nitrile in 65 ml of acetone and 3.25 ml of 4M hydrochloric acid was stirred at 40° C. for 2 h. Work-up as described in Example 11e produced, after chromatography, 0.7 g of 4'-[(11β,17α)-17,23-epoxy-3-oxo-19,24-dinorchola-4,20-dien-11-yl]-1,1'-biphenyl-4-carbonitrile. M.p. 177° C.

EXAMPLE 31 a. A mixture of 2.2 g of the triflate of Example 29a, 32 ml of toluene, 15 ml of ethanol, 0.59 g of diethyl (3-pyridyl) borate, 0.4 g of lithium chloride, 0.27 q of tetrakis (triphenylphosphine)palladium(0) and 6 ml of a 2M aqueous sodium carbonate solution was refluxed for 2.5 h. After cooling, ethyl acetate and brine were added and the layers separated. The organic layer was washed with brine, dried over magnesium sulfate and the solvent was removed under reduced pressure. The residue was chromatographed to afford 2 g of (11β,17α)-17,23-epoxy-11-[4-(3-pyridinyl) phenyl]-19,24-dinorchola-5,20-dien-3-one cyclic 1,2-ethanediyl acetal.

b. A mixture of 2 g of this acetal, 100 ml of acetone and 5 ml of 4M hydrochloric acid was stirred for 2 h at 40° C. Work up as described in Example 11e gave 1 g of (11β,17α)-17,23-epoxy-11-[4-(3-pyridinyl)-phenyl]-19,24-dinorchola-4,20-dien-3-one. M.p. 255° C.

EXAMPLE 32 a. To a mixture of 1.2 g of (11β,17α)-17,23-epoxy-11-(4-methoxyphenyl)-19,24-dinorchola-4,20-dien-3-one (Example 26e), 30 ml of tetrahydrofuran, 0.4 ml of trimethylorthoformate, and 3.3 ml of methanol were added 0.6 ml of boron trifluoride etherate at 0° C. After stirring for 6 h at this temperature, pyridine was added and the mixture was evaporated under reduced pressure. The residue was chromatographed to afford 1 g of methyl dienol ether.

b. To a solution of 1 g of this methyl dienol ether in 10 ml of acetonitrile were added 800 mg of palladium(II)acetate. The mixture was stirred for 16 h at room temperature and subsequently filtered over celite. After washing the celite with ethyl acetate, the filtrate was concentrated under reduced pressure. The residue was purified by chromatography to give 350 mg of (11β,17α)-17,23-epoxy-11-(4-methoxyphenyl) -19,24-dinorchola-4,6,20-trien-3-one. M.p. 225° C.

EXAMPLE 33 a. To a solution of 1 g of the acetal of Example 26d in 10 ml of dichloromethane containing 0.1 ml of pyridine were added at 0° C. 0.1 ml of hexachloro-acetone followed by 1 ml of 30% hydrogen peroxide. The mixture was stirred at room temperature for 7 days. After this period, water and dichloromethane were added; the layers were separated, and the organic layer was washed with a sodium thiosulfate solution and water. The solution was dried over magnesium sulfate, the solvent was evaporated, and the residue chromatographed to afford 0.53 g of the intermediate 5α,6α-epoxide. M.p. 223° C.

b. To a solution of 0.53 g of this epoxide in 3 ml of tetrahydrofuran were added 4.7 ml of a methyl-magnesium chloride solution (3M in tetrahydrofuran) at -20° C. The mixture was stirred for 16 h at room temperature, poured slowly into an ice-cold ammonium chloride solution, and extracted with ethyl acetate. The organic layer was washed with brine and dried over magnesium sulfate and the solvent was removed under reduced pressure. The crude (5α,6β,11β,17α) -17,23-epoxy-5-hydroxy-11-(4-methoxyphenyl)-6-methyl-19,24-dinorchola-20-en-3-one cyclic 1,2-ethanediyl acetal (0.55 g) was used in the next steps without further purification.

c. A mixture of 0.2 g of this acetal, 0.5 ml of 4M hydrochloric acid and 10 ml of acetone was stirred for 2 h at 40° C. Work-up as described in Example 26e afforded, after chromatography, 0.12 g of (6α,11β,17α)-17,23-epoxy-11-(4-methoxyphenyl)-6-methyl-19,24-dinorchola-4,20-dien-3-one. M.p. 209° C.

d. A mixture of 0.3 g of the acetal of b, 15 ml of acetone and 1.5 ml of 4M hydrochloric acid was stirred for 2 h at 0° C. Work-up as described in Example 26e afforded after chromatography, 0.25 g of (5α,6β,11β,17α)-17,23-epoxy-5-hydroxy-11-(4-methoxy-phenyl)-6-methyl-19,24-dinorchol-20-en-3-one.

e. A mixture of 0.15 g of the 5-hydroxy derivative of d, 6 ml of ethanol and 0.3 ml of 0.1M sodium hydroxide was stirred for 4.5 h at room temperature. Subsequently, the solution was poured into a saturated ammonium chloride solution and extracted with ethyl acetate. The organic layer was washed with brine, dried over magnesium sulfate, and the solvent removed under reduced pressure. Chromatography afforded 0.08 g of (6β,11β,17α)-17,23-epoxy-11-(methoxyphenyl)-6-methyl-19,24-dinorchola-4,20-dien-3-one. M.p. 201° C.

EXAMPLE 34

(17α)-17,24-epoxy-13-ethyl-18,19-dinorchola-4,20-dien-3-one was prepared from 3-ethoxy-13-ethylgona-3,5-dien-17-one as follows:

a. A solution of 20.2 g of 2-bromo-5-trimethylsilyloxy-1-pentene in 340 ml of dry ether was cooled to -78° C., and 100 ml of a tert-butyllithium solution (1.7M in pentane) were added dropwise. After 15 min, 21.35 g of the steroid mentioned above were added; the mixture was then allowed to warm to 0° C. over a period of 2 h. Subsequently, the reaction mixture was poured into a saturated aqueous solution of ammonium chloride, which was extracted three times with ethyl acetate. The combined extracts were washed with a solution of sodium bicarbonate and with brine, dried over sodium sulfate, and concentrated under reduced pressure to afford 2.89 g (88%) of the desired (17α) -3-ethoxy-13-ethyl-24-trimethylsilyloxy-18,19-dinorchola-3,5,20-trien-17-ol, which was used in the next step without further purification.

b. 28.9 g of the alcohol described above were dissolved in a mixture of 1100 ml of acetone, 11 ml of water and 11 ml of concentrated hydrochloric acid, and the mixture stirred at room temperature for 2 h. Sodium bicarbonate solution was then added, and the acetone removed under reduced pressure. The residue was extracted three times with ether; the combined extracts were washed with bicarbonate solution and with brine, dried over sodium sulfate, and concentrated under reduced pressure. The residue was chromatographed to afford 7.86 g (33%) of (17α)-13-ethyl-17,24-dihydroxy-18,19-dinorchola-4,20-dien-3-one.

c. To a solution of 3.27 g of the diol obtained in the previous step and 5.8 ml of s-collidine in 18 ml of dry dichloromethane were dropwise added 1.05 ml of methanesulfonyl chloride. The mixture was then stirred at room temperature for 45 min, after which period the reaction mixture was poured into water; this was extracted three times with ethyl acetate; the combined extracts were washed with water (four times) and with brine, and dried over sodium sulfate. The solvent was removed by evaporation under reduced pressure, and the residue taken up in a mixture of 5.8 ml of s-collidine and 40 ml of dry toluene. The solution was refluxed for 1 h, after which it was poured into water. Extraction with ethyl acetate, washing of the combined extracts with brine, drying over sodium sulfate and evaporation of the solvent left a residue which was purified by chromatography to afford 2.1 g (67%) of (17α) -17,24-epoxy-13-ethyl-18,19-dinorchola-4,20-dien-3-one. M.p. 167.1° C. $[\alpha]_D^{20}$=-34.8° (c=1.0, chloroform).

EXAMPLE 35

In a similar manner as in Example 34 were prepared:

(17α)-17,24-epoxy-19-norchola-4,20-dien-3-one from 3-ethoxyestra-3,5-dien-17-one. M.p. 170.5° C. $[\alpha]_D^{20}$=-31° (c=1.0, chloroform).

(17α)-17,24-epoxy-11-methylene-19-norchola-4,20-dien-3-one from 11-methyleneestr-4-ene-3,17-dione 3-cyclic 1,2-ethanediyl acetal. M.p. 177° C. $[\alpha]_D^{20}$=+86° (c=1.0, chloroform).

(17α)-17,24-epoxy-11-methylene-19-norchola-4,15,20-trien-3-one from 11-methyleneestra-4,15-diene-3,17-dione 3-cyclic 1,2-ethanediyl acetal. M.p. 194.5° C. $[\alpha]_D^{20} = +2.8°$ (c=1.0, chloroform).

(11β,17α)-17,24-epoxy-11-methyl-19-norchola-4,20-dien-3-one from (11β)-11-methylestr-4-ene-3,17-dione 3-cyclic 1,2-ethanediyl acetal. M.p. 200° C. $[\alpha]_D^{20} = +4.4°$ (c=1.0, chloroform).

(11β,17α)-17,24-epoxy-11-(4-methoxyphenyl)-19-norchola-4,20-dien-3-one from (11β)-11-(4-methoxyphenyl)estr-5-ene-3,17-dione cyclic 3-(11,2-ethanediyl acetal). M.p. 169° C.

EXAMPLE 36 a. (17α)-17-hydroxy-24-trimethylsilyloxy-19-norchola-5(10),9(11),20-trien-3-one cyclic 1,2-ethanediyl acetal was prepared from 44 g of estra-5(10),9(11)-dien-3,17-dione cyclic 3-(1,2-ethanediyl acetal) [A. Belanger et al. Steroids 37 (1981), 361–383] as described in Example 34a.

b. The crude product of the previous step was dissolved in 500 ml of tetrahydrofuran and added to a suspension of 22 g of potassium fluoride and 2.6 g of 18-crown-6 in 250 ml of tetrahydrofuran. After stirring at room temperature for 1 h, water and ethyl acetate were added, the layers were separated, and the organic layer was washed with brine and dried over magnesium sulfate. Concentration in vacuo followed by chromatography afforded 21 g of estra-5(10),9(11)-dien-3,17-dione cyclic 3-(1,2-ethanediyl acetal) and 25 g of (17α)-17,24-dihydroxy-19-norchola-5(10),9(11),20-trien-3-one 3-cyclic 1,2-ethanediyl acetal.

c. To a solution of 25 g of (17α)-17,24-dihydroxy-19-norchola-5(10),9(11),20-trien-3-one cyclic 1,2-ethanediyl acetal in 107 ml of dichloromethane and 54 ml of pyridine were added 6.4 ml of methanesulfonyl chloride at 0° C., and stirring was continued at room temperature for 2 h. The reaction mixture was poured into a sodium hydrogen carbonate solution, ethyl acetate was added and the layers were separated. The organic layer was washed with brine, dried over magnesium sulfate and the solvent was removed under reduced pressure affording 35 g of crude (17α)-17-hydroxy-24-methanesulfonyloxy-19-norchola-5(10),9(11),20-trien-3-one cyclic 1,2-ethanediyl acetal.

d. 35 g of this crude mesylate were dissolved in 275 ml of toluene and 40 ml of collidine and the solution was refluxed for 2 h. Subsequently, the reaction mixture was poured into a sodium hydrogen carbonate solution, ethyl acetate was added and the layers were separated. The organic layer was washed with brine and dried over magnesium sulfate. After concentration in vacuo, chromatography afforded 15 g of (17α)-17,24-epoxy-19-norchola-5(10),9(11),20-trien-3-one cyclic 1,2-ethanediyl acetal.

e. A mixture of 3.8 g of the above-mentioned acetal, 0.3 ml of pyridine, 1 ml of α,α,α-trifluoroacetophenone, 57 ml of dichloromethane and 13.5 ml of 30% hydrogen peroxide was stirred for 3 days at room temperature. Subsequently, dichloromethane and water were added, the layers were separated, and the organic layer was washed with a sodium thiosulfate solution and water. After drying over magnesium sulfate and evaporation of the solvent, the residue was chromatographed to give 3 g of the intermediate 5α,10α-epoxide.

f. To a solution of [(4-dimethylamino)phenyl] magnesium bromide (prepared from 1.5 g of 4-bromo-N,N-dimethylaniline and 185 mg of magnesium) in 6 ml of tetrahydrofuran were added 21 mg of copper(I)chloride at room temperature. Subsequently, 623 mg of the 5α,10α-epoxide of Example 34e in 5 ml of tetrahydro-furan were added and stirring was continued for 1 h. The mixture was poured into an ammonium chloride solution and extracted with ethyl acetate. After washing with water, the organic layer was dried over magnesium sulfate and concentrated under reduced pressure. The residue was chromatographed to afford 727 mg of the intermediate (5α,11β,17α)-11-[4-(dimethylamino)phenyl]-17,24-epoxy-5-hydroxy-19-norchola-9,20-dien-3-one cyclic 1,2-ethanediyl acetal. M.p. 179° C.

g. 562 mg of the acetal of 34f in 5 ml of 70% acetic acid were heated for 1 h at 50° C. After cooling to room temperature the mixture was neutralized with sodium hydrogen carbonate and extracted with ethyl acetate. After drying over magnesium sulfate, the solvent was evaporated and the residue chromatographed to give 447 mg of (11β,17α)-11-[4-(dimethylamino)phenyl]-17,24-epoxy-19-norchola-4,9,20-trien-3-one. M.p. 158° C.

EXAMPLE 37

In an analogous manner as described in Example 36 were prepared:

(11β,17α)-17,24-epoxy-11-(4-methoxyphenyl)-19-norchola-4,9,20-trien-3-one. M.p. 116° C.

(11β,17α)-11-(4-acetylphenyl)-17,24-epoxy-19-norchola-4,9,20-trien-3-one. M.p. 154° C.

(11β,17α)-17,24-epoxy-11-(4-methylthiophenyl)-19-norchola-4,9,20-trien-3-one. M.p. 153° C.

(11β,17α)-17,24-epoxy-11-[4-(1-methylethyl)phenyl]-19-norchola-4,9,20-trien-3-one. M.p. 130° C.

We claim:

1. A compound having the formula:

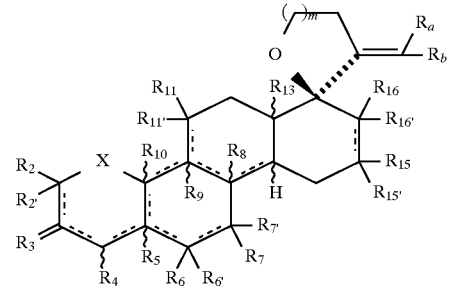

wherein:

$R_a$ and $R_b$ are independently selected from the group consisting of hydrogen, methyl, and halogen;

m is 1 or 2;

X is $CHR_1$ or a bond;

$R_1$ is H, $CH_3$, CN, OH, Oacyl, F, spirocyclopropyl; or together with $R_2$ or $R_{10}$ is $CH_2$, $CF_2$, or $OC(CH_3)_2O$; or together with $R_{11}$ is $CH_2O$;

$R_2$ is H, alkyl, $CH_2OH$, CN, OH, Oacyl, F, or spirocyclopropyl; or together with $R_1$ or $R_3$ is a group indicated in the definitions of $R_1$ and $R_3$, respectively; or together with $R_{10}$ is $CH_2$; or together with $R_{2'}$ is =CH—R, wherein R is H, OH, oalkyl, or Oacyl;

$R_{2'}$ is H, alkyl, or CN; or together with $R_2$ is a group indicated in the definition of $R_2$;

$R_3$ is $H_2$, O, NOH, NOalkyl, NOacyl, (H,OH), (H,Oacyl), (O,Oalkyl), (H,Ocycloalkyl), or 1-pyrrolidinyl; or (O,alkynyl) when X is a bond; or $R_2$ and $R_3$ together with C2 and C3 of the steroid skeleton form an oxazole:

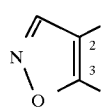

or a diazole:

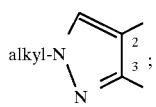

R₄ is H, alkyl, halogen, CN, N₃, OH, phenylmethyl, phenylthiomethyl, methylthio, or alkylcarbonylthio;

R₅ is H or OH;

One of R₆ and R₇ is H, alkyl, CF₃, CH₂F, OH, halogen, CN, Oalkyl, Oacyl, Sacyl, CH₂OH, NO₂, COOalkyl, OSO₂alkyl, or spirocyclopropyl, and the other is H; or R₆ together with R₇ is CH₂, CF₂, O, or CHClCHCl; or R₆ together with R6' is CH₂ when R₇ is H; or R₇ together with R₇' is CH₂ or CF₂ when R₆ is H;

R₆' is H; or H or alkyl when R₆ is alkyl; or H or halogen when R₆ is halogen; or together with R₆ is a group indicated in the definition of R₆; or H or F when R₆ and R₇ together are CF₂;

R₇' is H; or H or alkyl when R₇ is alkyl; or H or halogen when R₇ is halogen; or together with R₇ is a group indicated in the definition of R₇;

R₈ is H or CH₃;

R₉ is H, halogen, OH, or methyl; or together with R₁₀ is CH₂ or O;

R₁₀ is H, alkyl, halogen-substituted alkyl, alkenyl, alkynyl, halogen, OH, OOH, OOacyl, Oalkyl, Oalkynyl, amino, alkyl-substituted amino, NHacyl, aminomethyl, alkyl-substituted aminomethyl, CHO, COOH, COOalkyl, CH₂OH, CH₂Oacyl, or CH₂CH₂OH; or together with R₁, R₉, or R₁₁, is a group indicated in the definition of R₁, R₉, or R₁₁ respectively; or together with C10, C9, C11 of the compound skeleton and R₁₁ is a 6-membered ring when R₁₁ is an aryl or heteroaryl;

R₁₁ is H, alkyl, cycloalkyl, alkenyl, alkynyl, phenylethyl, arylethynyl, heteroarylethynyl, halogen-substituted alkyl, alkyl-substituted aminoalkyl, halogen, CH₂OCH₃, OH, OOH, Oalkyl, Oacyl, SH, Salkyl, N₃, Si(CH₃)₂, aryl, or heteroaryl; or R₁₁ together with R₁₁' is CH₂, CF₂, or CHF; or together with R₁₀ is OC═O or OCHF; or together with R₁ is OCH₂; or together with R₁₃ is OCH₂ or CH₂CH₂CH₂;

R₁₁' is H, alkyl, cycloalkyl, alkenyl, alkynyl, phenylethyl, arylethynyl, heteroarylethynyl, halogen-substituted alkyl, alkyl-substituted aminoalkyl, halogen, CH₂OCH₃, OH, OOH, Oalkyl, Oacyl, SH, Salkyl, N₃, Si(CH₃)₂, aryl, or heteroaryl; or R₁₁' together with ₁₁ is a group indicated in the definition of R₁₁; or together with R₁₃ is CH₂CH₂CH₂ when R₁₁ is H;

R₁₃ is H, alkyl, alkenyl, alkynyl, fluoro-substituted alkyl, phenyl, or cycloalkyl; or R₁₃ together with R₁₁, R₁₁', or R₁₆ is CH₂CH₂CH₂;

One of R₁₅ and R₁₆ is H, OH, Oalkyl, Oacyl, halogen, alkyl, or spirocyclopropyl, and the other is H; or R₁₅ together with R₁₆ is CH₂ or CClF;

R₁₅' is H; or together with R₁₅ is CH₂ or F₂ when R₁₆ is H;

R₁₆' is H; or together with R₁₆ is CH₂ or F₂ when R₁₅ is H;

and wherein the twitched lines represent an α or β bond; and the dotted lines represent up to four optional non-adjacent bonds;

or pharmaceutically acceptable salts thereof.

2. A process for the preparation of the compound of claim 1 by treating any 17-keto compound (reactive substituents of which are protected in a manner as usual for the protection of reactive groups) with a) alkylOCLi═C═CH₂, wherein alkyl is a lower alkyl, after which the 17-allenyl derivative obtained is treated with a base in a suitable solvent or with silver nitrate to obtain the alkyl enol ether of a furan ring, carbon atom 2 of which is carbon atom 17 of the compound skeleton, which after acid treatment gives a furan-3-one ring, of which carbon atom 2 is carbon atom 17 of the compound skeleton, when necessary followed by reprotection of cleaved groups, after which a Wittig, Wittig-Horner, or similar reaction with W-CHR_aR_b is performed, wherein R_a and R_b have the previously given meanings, and W is a group suitable for a Wittig(like) or Peterson reaction; or b) R_aR_bC═CLi—CH₂—CH₂—CH₂—OSi(alkyl)₃, wherein R_a, R_b and alkyl have the previously given meanings, followed by acid hydrolysis to give the 17,24-dihydroxy compound, after which the 24-hydroxy group is converted into a leaving group, followed by ring closure to a 17-spiroether derivative;

after which the remaining protective groups, when present, are removed and the compound obtained is optionally converted into a pharmaceutically acceptable salt.

3. A pharmaceutical preparation comprising the compound according to claim 1 and pharmaceutically acceptable auxiliaries.

4. A method for contraception in a patient, comprising administering the compound of claim 1 to the patient.

* * * * *